United States Patent
Widlund

(10) Patent No.: US 6,230,374 B1
(45) Date of Patent: *May 15, 2001

(54) FASTENER DEVICE FOR AN ABSORBENT ARTICLE

(76) Inventor: Urban Widlund, Päronvägen 5, S-435 43, Mölnlycke (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,146
(22) PCT Filed: Jun. 27, 1996
(86) PCT No.: PCT/SE96/00855
    § 371 Date: Jan. 5, 1998
    § 102(e) Date: Jan. 5, 1998
(87) PCT Pub. No.: WO97/02799
    PCT Pub. Date: Jan. 30, 1997

(30) Foreign Application Priority Data

Jul. 7, 1995 (SE) .................................. 9502494

(51) Int. Cl.[7] ................................... A41F 13/56
(52) U.S. Cl. .................. 24/577; 24/579.1; 24/697.1; 24/697.2
(58) Field of Search .................. 604/389–391; 24/442, 452, 575, 579.1, 697.1, 697.2, 577

(56) References Cited

U.S. PATENT DOCUMENTS

| | | | |
|---|---|---|---|
| 147,691 | * | 2/1874 | Richard . |
| 498,913 | * | 6/1893 | Fiske . |
| 770,535 | * | 9/1904 | Phillips . |
| 1,253,521 | * | 1/1918 | Ozanne . |
| 1,500,153 | * | 7/1924 | Reed . |
| 2,833,016 | * | 5/1958 | Williams . |
| 3,214,816 | * | 11/1965 | Mathison . |
| 3,403,429 | * | 10/1968 | Smith . |
| 3,875,837 | | 4/1975 | Dussaud . |
| 4,670,960 | * | 6/1987 | Provost . |
| 5,060,348 | * | 10/1991 | MKoshier . |
| 5,269,776 | | 12/1993 | Lancaster et al. . |
| 5,312,387 | * | 5/1994 | Rossini et al. . |
| 5,399,219 | * | 3/1995 | Roessler et al. . |
| 5,487,809 | * | 1/1996 | Goulait et al. . |
| 5,603,708 | * | 2/1997 | Seth . |
| 5,768,754 | * | 6/1998 | Armstrong . |
| 5,961,761 | * | 10/1999 | Heindel et al. . |

FOREIGN PATENT DOCUMENTS

| | | |
|---|---|---|
| 384 317 | 5/1976 | (CH) . |
| 0 215 408 A2 | 3/1987 | (EP) . |
| 0 233 704 A2 | 8/1987 | (EP) . |

(List continued on next page.)

Primary Examiner—James R. Brittain
(74) Attorney, Agent, or Firm—Burns, Doane, Swecker & Mathis, L.L.P.

(57) ABSTRACT

The present invention relates to a method of manufacturing fastener elements for fastening devices that are intended to be affixed to side-parts of an absorbent article of the kind which includes a central part and front and rear side-parts that project out from respective sides of the central part, so as to enable the front and rear side-parts on one and the same side of the central part of the article to be joined together. According to the invention, a central, longitudinally extending, wave-shaped slit is made in a material web which includes at least one continuous row of fastening devices or a continuous string of fastener devices or fastener-device blanks which extends in the longitudinal direction of the material web. Transverse slits are made on both sides of the material web up to the region of the wave-shaped slit, these transverse slits being mutually spaced in the longitudinal direction of the web at a continuously repeated spacing sequence. The invention also relates to fastener-device elements manufactured in accordance with the method.

19 Claims, 3 Drawing Sheets

FOREIGN PATENT DOCUMENTS

| | | |
|---|---|---|
| 0 262 447 A2 | 4/1988 | (EP) . |
| 0 274 752 A2 | 7/1988 | (EP) . |
| 0 274 753 A2 | 7/1988 | (EP) . |
| 2 286 762 | 8/1995 | (GB) . |
| 2 296 179 | 6/1996 | (GB) . |

* cited by examiner

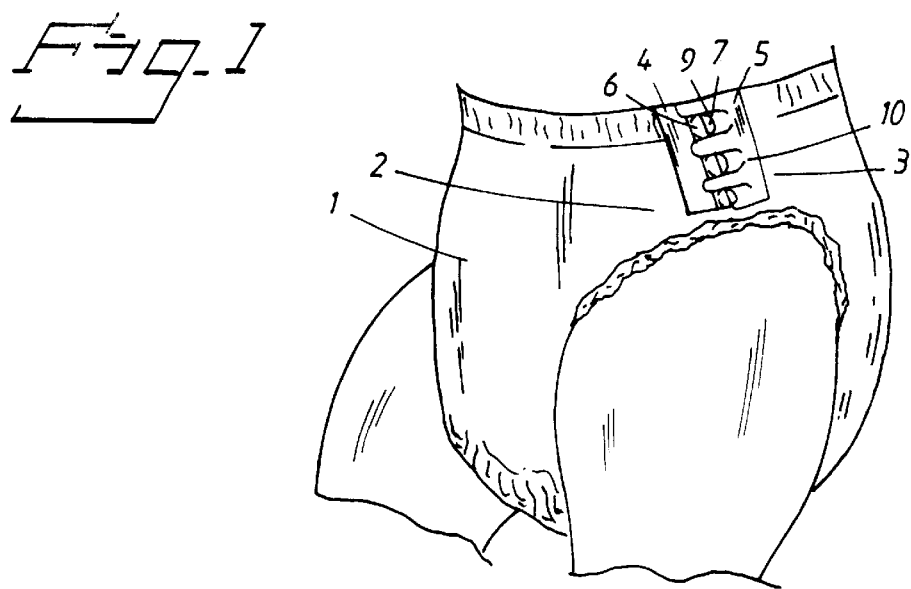
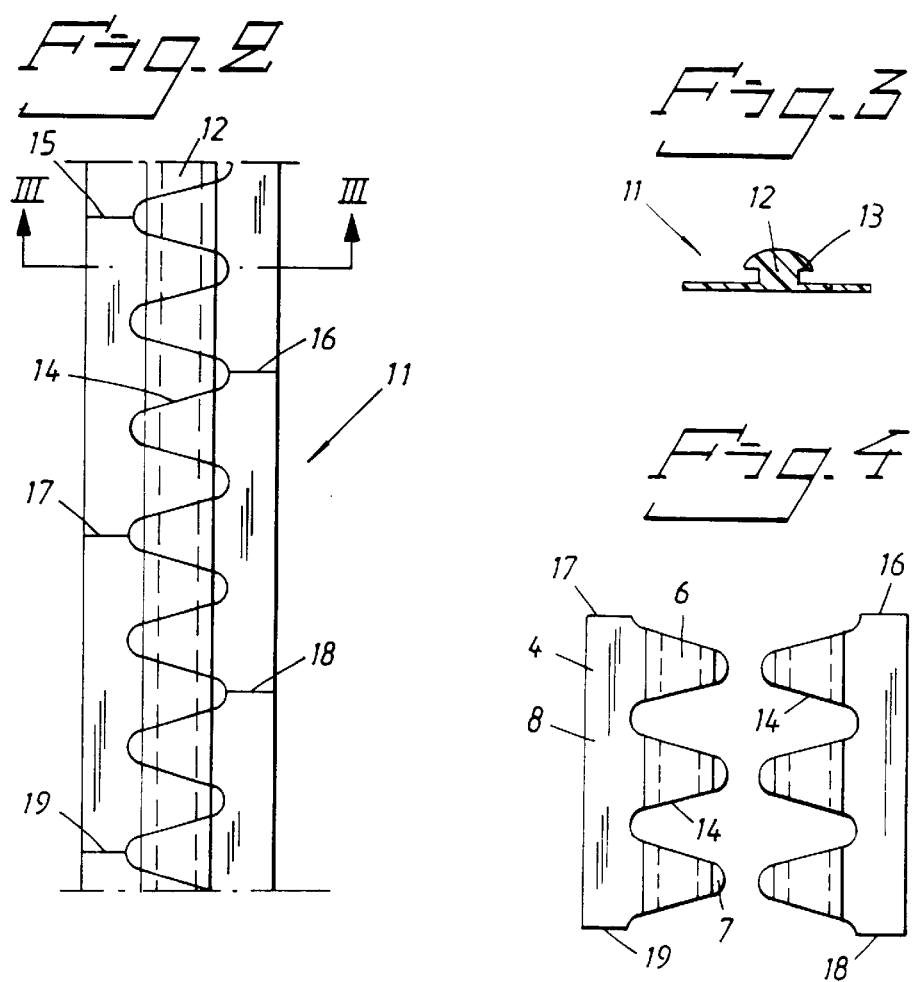

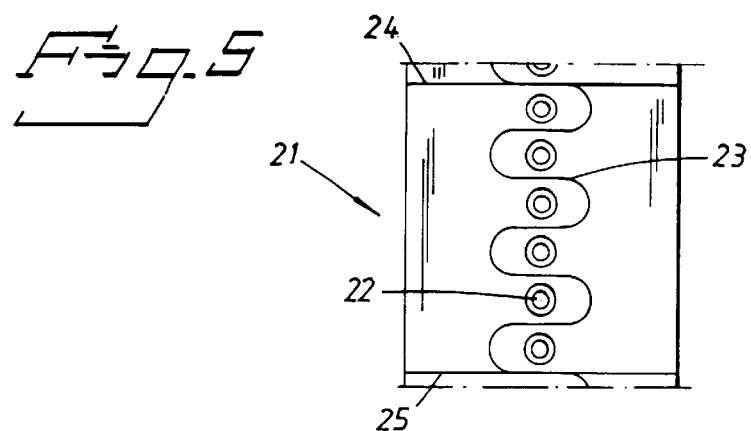
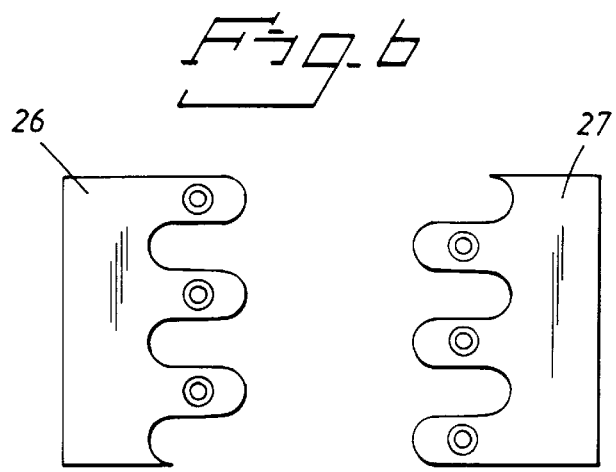
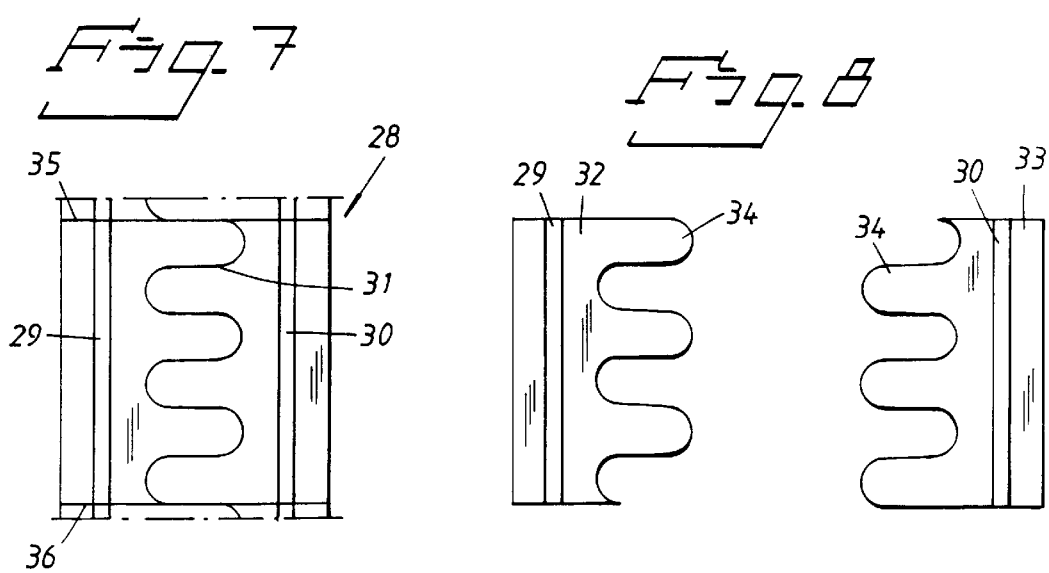

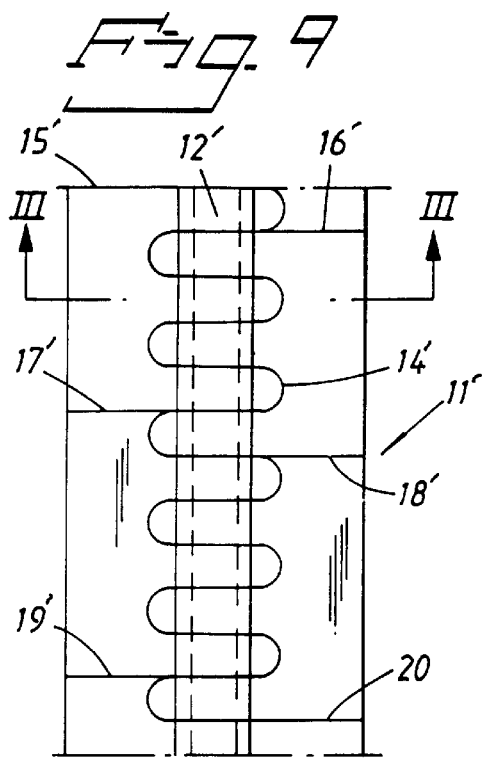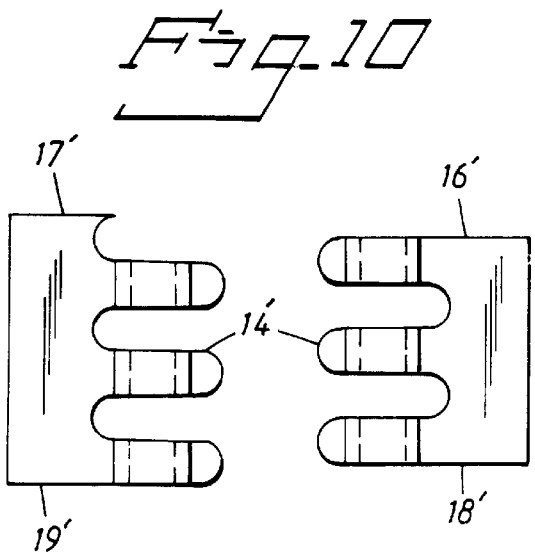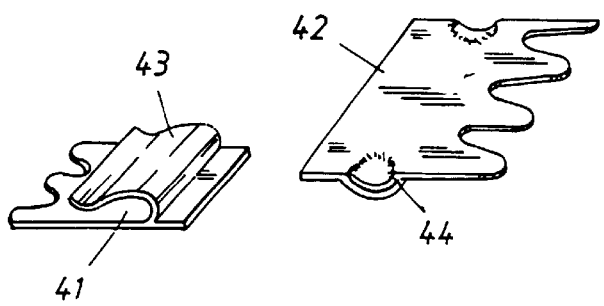

US 6,230,374 B1

FASTENER DEVICE FOR AN ABSORBENT ARTICLE

FIELD OF THE INVENTION

The present invention relates to a method of manufacturing fastener-device elements which are intended to be fastened to side-parts of an absorbent article of the kind which includes a central part and front and rear side-parts that project out from said central part, so as to enable front and rear side parts to be mutually joined on one and the same side of the central part of said article.

BACKGROUND OF THE INVENTION

The front and rear sides of a donned diaper are normally fastened together with the aid of fastener tabs. Although such adhesive fasteners have many good points, they also have certain drawbacks, such as their sensitivity to contaminants, their tendency to fasten in the "wrong" place, and so on. It has been suggested in recent times that these adhesive fasteners should be replaced with mechanical fasteners, such as press studs or the like; see for instance EP-A2 0 262 447 and U.S. Pat. No. 5,269,776.

SUMMARY OF THE INVENTION

A general object of the present invention is to provide elements for such fastener devices, essentially with no waste of material and in a manner which will enable application of the fastener-device elements to a diaper to be integrated readily in continuous diaper manufacturing processes. Another object of the invention is to enable such fastener-device elements to be produced from rolls of material. A further object of the invention is to improve the flexibility of this type of fastener-device element while retaining a large anchorage surface.

These objects are achieved in accordance with the invention with a method of the kind defined in the introduction that is characterized by making a central, longitudinally extending wave-like slit or cut in a material web which includes at least one row of fastener devices which extend in the longitudinal direction of the web or alternatively at least two continuous strings of fastener devices or at least one string of fastener-device blanks extending in the longitudinal direction of the web, and by making transversal slits which connect with said wave-shaped slit on both sides thereof, said transverse slits being mutually spaced from one another at a continuously repeated distance sequence in the longitudinal direction of the web.

According to one preferred embodiment the wave-shaped slit is made so that the wave has a constant amplitude and shape in a web of material that has one single centre string of fastener-device blanks, said transversal slit being extended transversely to a point beyond the string of fastener-device blanks on both sides thereof. The transverse slits' on one side of the centre line of the wave-shaped slit terminate in the wave crests of the undulating slit, while the transverse slits on the other side of said centre line terminate in the wave troughs of said slit. Furthermore, the distance between mutually sequential transverse slits on one and the same side of the wave-shaped section is such that each piece obtained on one side of said wave-shaped slit by slitting the web will include the same number of wave crests as the number of wave troughs in each piece produced on the other side of said longitudinal centre line.

According to another embodiment of the invention, adjacent transverse slits on both sides of the wave-shaped slit pass through the same points on the longitudinal symmetry line of the wave-shaped slit and the transverse slits are spaced equidistantly in the longitudinal direction. The web also has a central, longitudinally extending row of mutually equidistant studs or buttons and the wave-shaped slit is caused to pass transversely beyond the row of studs on both sides thereof while, at the same time, causing the longitudinal centre line of the wave-shaped slit to coincide with the longitudinal centre line of the stud or button row.

The invention also relates to fastener-device elements that are intended to be fastened to the side-parts of an absorbent article of the kind which includes a central part and front and rear side-parts projecting therefrom, so as to enable the front and the rear side-parts to be joined together on the same side of the central part of the article, said element including at least one continuous row or string of fastener devices, characterized in that each fastener-device element along one side parallel with the row or the string of fastener devices includes a row of outwardly projecting tongues. Such an element has great flexibility and also a large anchorage area.

According to one preferred embodiment of the invention, the side of the element that contains the tongues has an undulating outer contour. Furthermore, each tongue in the row of tongues includes a stud or button and the row of studs or buttons extends along the longitudinal centre line of the undulations that are delimited by the side containing the tongues. The buttons or studs extend over the full width of the tongues.

According to one variant, the row or the string of fastener devices extends on one side of the tongues.

BRIEF DESCRIPTION OF THE DRAWINGS

The invention will now be described in more detail with reference to the accompanying drawings, in which FIG. 1 is a schematic view of a donned diaper that is provided with fastener devices according to a first embodiment of the invention;

FIG. 2 s a view from above of a piece of web-like material intended for the manufacture of fastener-device elements for the front side-part of the diaper shown in FIG. 1;

FIG. 3 is a section view taken on the line III—III in FIG. 2;

FIG. 4 is a view from above of two fastener-device elements spaced mutually apart;

FIGS. 5 and 6, FIGS. 7 and 8, FIGS. 9 and 10 are views of a fastener device element similar to the views of FIGS. 2 and 4 respectively according to further embodiments of the invention; and FIGS. 11–13 show alternative embodiments of inventive fastener devices that include hook-like fastener means.

DETAILED DESCRIPTION OF THE PREFERRED EMBODIMENTS

FIG. 1 shows a diaper 1 which has been donned by the wearer with the diaper placed around the wearer's bottom and the rear and front parts 2 and 3 of the diaper fastened together with the aid of coacting fastener-device elements 4 and 5 attached to the front and the rear parts of the diaper respectively. Only the left side-parts 2 and 3 of the front and the rear of the diaper are shown in the Figure. The left part of FIG. 4 shows one such fastener-device element 4 in larger scale. The fastener-device element 4 includes a row of upstanding studs 6 which are attached to a row of tongues 7 that project laterally outwards from a generally rectangular base part 8. The fastener-device element 4 is made from a pliable material, for instance a pliable thermoplastic material, and is attached to the outside of the front side-part 2 of the diaper in some suitable manner, for instance is welded or glued thereto. The fastener element 5 that coacts with the fastener element 4 includes a row of eyes 9 which extend laterally from the base-part 10 and which are located at the same distance from one another as the spacing between the studs 6 in the row of studs on the element 4. In order to enable the eyes 9 to be threaded easily over the studs 6, the outer ends of the eyes are conveniently joined together by means of a common cross-piece (not shown) so as to enable all eyes to be threaded on all studs simultaneously. This cross-piece may have the form of an elongated two-layer laminate with the outer parts of the eyes fastened between the laminating layers.

The fastener element to be fastened to the front side-parts of the diapers are manufactured from a web-like material 11 which includes a central, outwardly projecting and longitudinally extending rib 12 having a rounded upper side and laterally projecting flanges 13, as illustrated in FIGS. 2 and 3. The fastener elements are produced from the material web by making in the web 11 a central, longitudinally extending wave-shaped slit 14 and a plurality of transverse slits 15, 16, 17, 18 and 19. The wave-shaped slit 14 has a sinusoidal wave shape and the transverse slits extend at right angles from respective sides of the web 11 to a respective wave trough on the left side of the slit 14 and a respective wave crest on the right side of said slit. The transverse slits 15, 17, 19 that extend from the left side of the web 11 as seen in FIG. 2 are displaced one and one-half wavelength in the longitudinal direction of the web in relation to adjacent transverse slits 16, 18 that extend from the right side of the web. The distances between the transverse slits that depart from the left side and the right side of the web 11 respectively are such that the number of wave crests between the left transverse slits 15, 17 and 17, 19 respectively are equal to the number of wave troughs between the transverse slits 16, 18 departing from the right side of the web. Slitting of the web in this way will result in pairs of fastener elements having mutually opposing tongues. One such pair of fastener elements is shown in FIG. 4, said pair of elements having been obtained by separating the left and the right pieces cut from the web 11 and thereafter displacing said parts longitudinally in relation to one another, such that the wave troughs of the left piece will lie opposite the wave troughs of the second piece, i.e. so that the tongues of the pair of fastener elements obtained by slitting the web will lie opposite one another. As shown in FIG. 1, the left fastener-device element is fastened to the left side-part of the diaper 1 and the right fastener-device element is fastened to the right side-part of said diaper.

The aforedescribed method enables the application of fastener-device elements to be integrated with the continuous crosswise production of diapers, in which the diaper blanks move along the process line with their longitudinal axis at right angles to the conveyor or conveyors on which the blanks are advanced through the line, by virtue of the fact that the right and the left side-parts of the diaper blanks on which the pairs of fastener-device elements are to be applied lie adjacent one another. This integration enables the web material shown in FIG. 2 to be slit on site at the place where the fastener-device elements obtained by the slitting operation are to be applied. For instance, the web material can be caused to move at right angles to the direction of movement of the underlying web of diaper blanks. When the right front side-part of a diaper blank is located opposite one of the right-hand pieces slit from the web material 11, this right-hand piece is pressed against the side-part of said diaper blank. Subsequent movement of the web of diaper blanks will then bring the left-hand front side-part of the blank to a position opposite one of the left-hand pieces slit from the material web 11 and this left-hand piece is pressed onto the left front side-part so as to be affixed therewith. Because the web material 11 has moved at right angles relative to the web of diaper blanks, the mutually opposing tongues 7 of the fastener-device elements can be positioned opposite one another, by moving the web material 11 at the appropriate speed. The aforedescribed fastener-device elements can thus be applied to the diaper blanks relatively easily without interfering with the diaper manufacturing process in any way.

The aforedescribed method also enables the application of fastener-device elements to be integrated with a continuous diaper manufacturing process in which the diapers are in the advanced in the direction of their length axis. For instance, when the diapers are advanced in their length direction, the material web 11 can be moved in the same direction as the web of diaper blanks and be divided along its length into two separate webs by making the wave-shaped cut along the length of the material web, whereafter individual fastener-device elements can be slit out and applied to the side-parts of respective diaper blanks.

FIGS. 9 and 10 illustrate an alternative method of slitting a material web, here referenced 11', similar to the material web 11 shown in FIGS. 2 and 3. In the case of this variant, the wave-shaped slit 14' has the form of a square wave with rounded crests and troughs and the transverse slits 15'–19' and 20 connect with the wave-shaped section 14' at straight parts of the square wave. Delimiting transverse slits are displaced relative to one another through one-half of a wavelength in the longitudinal direction.

It will be understood that fastener-device elements fastened to the rear side-parts of the diaper and coacting with the aforesaid pair of stud-provided fastener-device elements can be manufactured in the same way from smooth web material, by forming a longitudinally extending row of stud holes in the material and then slitting or cutting the material web in the same manner as that described above.

FIGS. 5 and 6 illustrate a second embodiment of an inventive method, in views similar to the views shown in FIGS. 2 and 4 respectively. As in the case of the first embodiment, fastener-device elements are manufactured by slitting a web of material 21, which in the illustrated case includes a central, longitudinally extending row of studs 22 instead of the web-mounted rib 12 shown in FIG. 2. A longitudinally extending wave-shaped slit 23 and transverse slits 24, 25 are made in the material web 21. As opposed to the embodiment earlier described with reference to FIGS. 2–4, the transverse slits made from each side of the material web are located opposite one another in the longitudinal direction of said web and are located at the same distance apart. FIG. 6 illustrates a pair of fastener-device elements 26, 27 with the elements shown separated from one another. As in the earlier case, the fastener-device element 26 shown on the left of the Figure is applied to the left front side-part of a diaper, while the element 27 shown on the right of the Figure is applied to the right front side-part of the diaper.

Application of the pairs of fastener-device elements 26, 27 manufactured from the material web 21 onto the diaper blanks can be integrated readily with the process line for lengthwise and crosswise diaper manufacture in essentially the same way as that described with reference to FIGS. 2–4.

FIGS. 7 and 8 illustrate schematically a third embodiment of the invention, wherein the only difference from the earlier described embodiments is that the material web 28 includes two longitudinally extending rows 29, 30 of fastener-device elements. The wave-shaped slit 31 is made between these rows 29, 30 and the transverse slits 35, 36 extend across the full width of the material web 28.

There are also produced in this case pairs of fastener-device elements 32, 33 which are intended to be fastened to the mutually opposing front side-parts of a diaper. The fastener-device elements are preferably applied so that the fastener devices will be located close to the edge of the side-part of the diaper, irrespective of whether the fastener devices are located on the outwardly projecting tongues or on the base part. For this reason, the fastener-device elements 32 shown on the left of FIG. 8 can, in this case, be applied to the right front side-part of a diaper while the element 33 shown on the right of the Figure can be applied to the left front side-part. Application can be effected in essentially the same way as that described above with reference to the other embodiments of pairs of fastener-device elements, but with the difference that the fastener-device element 32 shown on the left of FIG. 8 is pressed fixedly onto the right front side-part of a diaper blank before the fastener-device element 33 shown on the right of the Figure is pressed fixedly onto the left side-part of the diaper blank when said side-part is positioned opposite the element 33 as a result of movement of the diaper blanks in the process line.

The fastener device string 29, 30 may be comprised of rows of studs or equivalent mechanical fasteners, although the strings may also consist in adhesive strings.

As an alternative to studs, the strings 29, 30 may consist in hook-shaped elements which extend along the full length of the fastener-device elements after having slit the material web. FIGS. 11 and 12 are cross-sectional views which show respectively two different examples of such coacting hook elements 37, 38 and 39, 40. The hooks 37 and 38 in FIG. 11 are held connected by the tension generated in the waist of the diaper formed by the diaper parts held together by said fastener devices, while the hooks 39, 40 of the FIG. 12 embodiment have a form which requires them to be resiliently deformed before they can be mutually disconnected from their article fastening position shown in FIG. 12. The hook connection shown in FIG. 12 is held intact by the spring action of the hooks 39, 40 even when no load acts on the connection.

FIG. 13 is a perspective view of two mutually coacting fastener-device elements 41, 42 of the type shown in FIG. 12 and having hook devices 43 and 44 respectively, shown separated in the Figure. As will be seen from the Figure, the fastener element 42 is longer than the fastener element 41. Furthermore, the short ends of the hook device 44 are fastened to adjacent edges of the base part of said fastener element. This ensures that when in their fastened state, the hooks 43, 44 will be secured against relative movement in the longitudinal direction of the elements.

All of the aforedescribed fastener-device elements have the form of essentially rectangular pieces which include tongues that project out from one side. As a result, the fastener elements will be more flexible in the plane of said elements than corresponding elements that have a rectangular shape but the same area. Such fastener elements can be affixed to the casing sheet of a diaper without stiffening the diaper unduly in the region where the fastener-device elements are attached while, at the same time, satisfying the requirement of a relatively large surface area for attachment of the fastener-device elements.

Furthermore, all studs or other types of fastener devices required on a diaper side-part are carried by one single fastener-device element, which is thereby relatively large. There is less risk of a child swallowing a fastener device, and the fastening devices can be secured more readily than in the case when each fastening device is attached individually to a diaper.

The described method of manufacturing such fastener-device elements is easy to carry out and, as earlier mentioned, application of the fastener-device element onto respective diapers can be integrated with a diaper manufacturing process line without disturbing the process. Furthermore, there is essentially no wastage of material when manufacturing the fastener-device elements, which is highly beneficial from the aspect of cost.

The described fastener-device elements may, of course, be applied to the rear side-parts of the diaper instead of its front side-parts as described above. Mechanical fastening devices other than studs, buttons and hooks may also be used, such as the male or female parts of Velcro® fasteners, for instance. The wave-shaped slit may have other wave shapes than those shown in the described exemplifying embodiments. The fastener-device elements may also be applied to other diaper-like products, such as incontinence guards, pants-type diapers (trainers) or pants-type sanitary napkins, and pants which include a diaper insert. The slits illustrated in the drawings have a regular wave shape, i.e. have constant amplitude and wave shape, although these parameters may, of course, be varied periodically. The invention therefore includes both regular and irregular wave shapes that are cutout in a periodically repeated pattern. It will be seen from FIG. 13 and its associated text that it may at times be desirable to provide fastener-device elements of mutually different lengths, in which case the cutting or slitting pattern will produce pairs of fastener elements that have different numbers of outwardly projecting tongues, this variant also being encompassed by the present invention. Furthermore, the choice of wave shape, fastener-device element and the pattern in which the transverse slits are made can be totally independent of one another. For instance, the string of fastener-device blanks in FIG. 2 may consist in a string of adhesive. These parameters can thus be freely combined. The invention is therefore limited solely by the contents of the following claims.

What is claimed is:

1. An absorbent article comprising:

a central part, front and rear side parts projecting out from respective sides of said central part, such that the central part, front and rear side parts on one and the same side of the central part of the article are joined together;

at least one fastener element attached to one of the front side part and the rear side part and at least one fastener device element attached to the other of the front side part and the rear side part such that said at least one fastener element is connectable to said at least one fastener device element;

said at least one fastener element lying in a plane and having at least one continuous row of fastener devices and a row of several identical tongues projecting outwardly in a wave shape and in the plane of the at least one fastener element perpendicular to the row of fastener devices with a fastener device on each tongue; and said fastener device element lying in a plane and having a plurality of identical tongues projecting outwardly in a wave shape and in the plane of the fastener device element and having a plurality of studs extending substantially perpendicularly from the plane of said tongues with a stud on each tongue;

wherein said studs of said fastener device element are engageable with said fastener devices of said fastener element to substantially maintain said front and rear side parts in a position to support said absorbent article on a wearer thereof.

2. The absorbent article as claimed in claim 1, wherein said tongues of said fastener elements and said fastener device elements have a plurality of wave crests and wave troughs.

3. The absorbent article as claimed in claim 2, wherein said tongues of said fastener elements each comprise the same number of wave crests and wave troughs.

4. The absorbent article as claimed in claim 2, wherein said tongues of said fastener device elements each comprise the same number of wave crests and wave troughs.

5. The absorbent article according to claim 1, wherein each of said tongues of said fastener elements and said fastener device elements is in the form of a square wave having rounded crests and troughs.

6. The absorbent article as claimed in claim 1, wherein said fastener devices comprise eyes which are configured to be threaded over the projections of said fastener device element.

7. The absorbent article as claimed in claim 1, wherein said studs extend along the longitudinal center line of the tongues of the fastener device element defined by an outer contour of said tongues.

8. The absorbent article as claimed in claim 1, wherein each of said studs extends over the full width of each said respective tongue of said fastener device element.

9. The absorbent article as claimed in claim 1, wherein each of said studs comprises a rib portion having flanges extending therefrom.

10. An absorbent article comprising:

a central part, front and rear side parts projecting out from respective sides of said central part, such that the central part, front and rear side parts on one and the same side of the central part of the article are joined together;

at least one fastener element attached to one of the front side part and the rear side part and at least one fastener device element attached to the other of the front side part and the rear side part such that said at least one fastener element is connectable to said at least one fastener device element;

said at least one fastener element lying in a plane and having at least one continuous row of fastener devices and a row of several identical tongues projecting outwardly in a wave shape and in the plane of the at least one fastener element perpendicular to the row of fastener devices with a fastener device on each tongue; and said fastener device element lying in a plane and having a plurality of identical tongues projecting outwardly in a wave shape and in the plane of the fastener device element and having a plurality of hook elements extending from the plane of said tongues with a hook element on each tongue;

wherein said hook elements of said fastener device element are engageable with said fastener devices of said fastener element to substantially maintain said front and rear side parts in a position to support said absorbent article on a wearer thereof.

11. The absorbent article as claimed in claim 10, wherein said tongues of said fastener elements and said fastener device elements have a plurality of wave crests and wave troughs.

12. The absorbent article as claimed in claim 11, wherein said tongues of said fastener elements each comprise the same number of wave crests and wave troughs.

13. The absorbent article as claimed in claim 11, wherein said tongues of said fastener device elements each comprise the same number of wave crests and wave troughs.

14. The absorbent article according to claim 10, wherein each of said tongues of said fastener elements and said fastener device elements is in the form of a square wave having rounded crests and troughs.

15. The absorbent article as claimed in claim 10, wherein said fastener devices comprise hook portions which are configured to be matingly connected to said hook elements of said fastener device element.

16. The absorbent article as claimed in claim 10, wherein said hook elements extend along the longitudinal center line of the tongues of said fastener device element defined by an outer contour of said tongues.

17. The absorbent article as claimed in claim 10, wherein each of said hook elements extends over the full width of each said respective tongue of said fastener device element.

18. The absorbent article as claimed in claim 10, wherein each of said fastener devices comprises a hook portion substantially similar to said hook elements of said fastener device elements, each of said hook portions extending from a respective one of said tongues.

19. The absorbent article as claimed in claim 10, wherein said fastener element comprises at least one hook device provided along an edge thereof for frictionally engaging a side of one of said hook elements.

* * * * *